(12) United States Patent
Suresh et al.

(10) Patent No.: US 11,781,947 B2
(45) Date of Patent: Oct. 10, 2023

(54) SYSTEM AND METHOD FOR AUTOMATED GROSS EXAMINATION OF TISSUES

(71) Applicant: Attili Venkata Satya Suresh, West Godavari (IN)

(72) Inventors: Attili Venkata Satya Suresh, West Godavari (IN); Anuradha Vutukuru, West Godavari (IN); Srikanth Sundara Sampara, Visakhapatnam (IN)

(73) Assignee: Attili Venkata Suresh, West Godavari (IN)

( * ) Notice: Subject to any disclaimer, the term of this patent is extended or adjusted under 35 U.S.C. 154(b) by 1543 days.

(21) Appl. No.: 15/777,909

(22) PCT Filed: Nov. 18, 2016

(86) PCT No.: PCT/IN2016/000275
§ 371 (c)(1),
(2) Date: May 22, 2018

(87) PCT Pub. No.: WO2017/085738
PCT Pub. Date: May 26, 2017

(65) Prior Publication Data
US 2018/0348092 A1    Dec. 6, 2018

(30) Foreign Application Priority Data
Nov. 21, 2015 (IN) .......................... 5663/CHE/2015

(51) Int. Cl.
| | |
|---|---|
| *G01N 1/06* | (2006.01) |
| *A61B 34/10* | (2016.01) |
| *A61B 8/08* | (2006.01) |
| *A61B 10/02* | (2006.01) |
| *A61B 34/30* | (2016.01) |

(Continued)

(52) U.S. Cl.
CPC .............. *G01N 1/06* (2013.01); *A61B 8/08* (2013.01); *A61B 10/02* (2013.01); *A61B 34/10* (2016.02); *A61B 34/30* (2016.02); *G16H 10/40* (2018.01); *A61B 2090/3612* (2016.02)

(58) Field of Classification Search
CPC . A61B 10/02; A61B 2090/3612; A61B 34/10; A61B 34/30; A61B 8/08; G01N 1/06; G16H 10/40
See application file for complete search history.

(56) References Cited

U.S. PATENT DOCUMENTS

| | | | | |
|---|---|---|---|---|
| 2012/0208184 A1* | 8/2012 | Ragan | ....................... | G01N 1/30 435/7.1 |
| 2013/0303895 A1* | 11/2013 | Littrup | ............... | A61B 17/3403 600/424 |

* cited by examiner

*Primary Examiner* — Mark D Remaly
(74) *Attorney, Agent, or Firm* — Barry Choobin; PATENT 360 LLC

(57) ABSTRACT

The various embodiments herein provide a system and method for automatic gross-examination of tissue samples. The apparatus is of cubicle shape comprising a bed where the specimen is placed, an ultrasound equipment mounted on top of cubicle box, a robotic arm mounted with a plurality of surgical blades, and a camera. The ultrasound technology is used to accurately understand the specimen, size and dimensions of a tumor that is studied. The robotic arm assisted surgical blades receive ultrasound output or camera output and accurately slice the specimen for further analysis. The information pertaining to gross-examination is stored in an external server connected to the apparatus and analyzed using artificial intelligence algorithms.

6 Claims, 9 Drawing Sheets

(51) Int. Cl.
*G16H 10/40* (2018.01)
*A61B 90/00* (2016.01)

SYSTEM AND METHOD FOR AUTOMATED GROSS EXAMINATION OF TISSUES

CROSS-REFERENCE TO RELATED APPLICATIONS

The embodiments herein claims the priority of the Indian Provisional Patent Application filed on Oct. 21, 2015 and subsequently postdated by one month to Nov. 21, 2015 with the number 5663/CHE/2015 and entitled, "AN AUTOMATED APPARATUS AND METHOD FOR GROSS EXAMINATION OF TISSUES", and the contents of which are included in entirety as reference herein. The embodiments herein claims the priority of the PCT application with serial number PCT/IN/2016/000275 filed on Nov. 18, 2016 and entitled "SYSTEM AND METHOD FOR AUTOMATED GROSS EXAMINATION OF TISSUES", and the contents of which are included in entirety as reference herein. The present application is a national phase application filed in continuation to the PCT application with serial number PCT/IN/2016/000275 filed on Nov. 18, 2016.

BACKGROUND

Technical Field

The embodiments herein are generally related to pathology grossing. The embodiments herein are particularly related to objective and reproducible inspection, image analysis and automated processing of pathological specimens. The embodiments herein are more particularly related to a completely automated apparatus with provision for human, technical, expert interface and a method for gross examination of tissue samples using image analysis techniques and artificial intelligence.

Description of the Related Art

To accurately diagnose various diseases and conditions, medical personnel remove one or more samples of tissue from the body of a patient. This process of harvesting tissue from the body is known as a biopsy. Once the tissue sample or samples are removed and sent to a pathological laboratory, the tissue is passed/processed through a series of procedures performed by a histo-technician and, ultimately, a pathologist, in order to diagnose the tissue. Once a tissue sample is removed from the body of a patient, the sample is typically placed into a specimen container containing a tissue fixative solution and then the container is transported to a pathological laboratory. The tissue undergoes a process known as "grossing-in" in the pathological lab during which a histo-technician retrieves the tissue sample from the container, typically cuts the tissue sample :into appropriate sizes for tissue processing, places individual samples into the appropriate sized small plastic tissue cassettes and assigns tracking numbers to each cassette. These tracking numbers are then logged into a tracking system used in the laboratory.

However, there is an immense need for the focus on grossing as grossing is a key step from where the entire story of pathological specimen processing begins. Grossing-in being the first step and most critical step involving histo-technicians/pathologists expertise and experience, any error at this stage severely and adversely affect the entire process of pathological testing and reporting.

All the current innovations till date have been dealing with post grossed specimen. The identification of key suspected or pathological areas is a crucial step in grossing; and this step is not currently standardized as it relies on visual inspection and palpation of specimen, both of which are highly subjective. Any error in identification of "accurate/relevant area" will lead to a completely erroneous report, which endangers the "pathological quality" there by affecting clinical decision-making for patient care.

Currently used innovations deal with post-grossed specimen. The grossing-in step is currently not standardized and largely relies on visual inspection and palpation of specimen, both of which are highly subjective. Any error in identification of accurate or relevant area leads to a completely erroneous report, which endangers the pathological quality there by effecting clinical decision making for patient care.

The current methods of pathological grossing are not effective for deeply embedded tumors in view of limitation of visual inspection and palpitation. The current method also poses a risk of accidental injury and/or infection to pathologist.

The average number of pathological specimens grossed globally is close to 50 Million with a huge deficiency of the trained histo-technicians, thereby making the step of Grossing highly vulnerable. The average time taken for the expert technician to gross the specimen is approximately thirty minutes. With this big gap of time, expertise and the quality of reporting, only a compromised report is expected to get.

Hence there is a need for a more objective, accurate, reproducible and automated way, which is driven by artificial intelligence technology and endorsed by trained pathologist before proceeding—using double check mechanism, for a gross examination of the tissue samples. There is also an immense need for the high speed and automated Grossing-in of specimens; a lymph node harvesting technology which is addressed with a help of imaging and robotics, as lymph node harvesting technology is an important event in the grossing in and as majority technicians are under-trained; reproducibility of results with minimum human interface and maximum accuracy; ability to serve the remote areas, which largely depend of telepathology, there grossing in errors lead to major misdiagnosis; ability to gross high volumes of specimens in limited time, with limited resources; accurate measures for preventing cross contamination with the help of automated and standardized procedures; digital documentation of the grossing process for review and corrections; and for better and uniform reporting with help of artificial intelligence.

Hence there is a need for an automated apparatus and method for gross examination of tissue samples. Further there is a need for an automated apparatus and method linked with Artificial Intelligence Engine for classification, probabilistic modelling, and advanced image analysis (image mining, speech recognition) processes. Still further there is a need for an automated apparatus and method provided with ultrasound technology and standardized imaging techniques for the gross examination of tissue samples method and to accurately understand the specimen, size and dimensions of the tumor. Yet there is a need for an automated apparatus and method for gross examination of tissue samples, to reduce a risk of accidental infection to pathologist/technicians during grossing, and to reduce a skin and eye infection due to exposure to formalin. Yet there is a need for an automated apparatus and method for grossly reducing the time with help of robotics, in view of the high volumes of the specimen loads.

The above mentioned shortcomings, disadvantages and problems are addressed herein, which will be understood by reading and studying the following specification.

OBJECTS OF THE EMBODIMENTS

The primary object of the embodiments herein is to provide an automated apparatus and method for gross examination of tissue samples.

Another object of the embodiments herein is to provide an automated apparatus and method connected to an artificial intelligence engine for classification, probabilistic modeling, advanced image analysis such as image mining and speech recognition processes during the gross examination of tissue samples.

Yet another object of the embodiments herein is to provide an automated apparatus and method with ultrasound or other imaging techniques for the gross examination of tissue samples to accurately understand the specimen, size, texture, margins, character, nodal status, and dimensions of the tumor.

Yet another object of the embodiments herein is to provide an automated apparatus and method that reduces a risk of accidental infection to pathologist or technicians during grossing, and reduces a skin and eye infection due to exposure to formalin.

Yet another object of the embodiments herein is to provide an automated apparatus and method with the ultrasound equipment and other imaging techniques to automate the process of cutting the specimen by providing output from ultrasound equipment and other imaging techniques to the robotic surgical blades to accurately slice a specimen for further analysis.

Yet another object of the embodiments herein is to provide an automated apparatus and method for more accurate pathological dissection, to get the samples of ideal/relevant areas for processing.

Yet another object of the embodiments herein is to provide an automated apparatus and method to increase accuracy and to reduce false-positive and false-negatives.

Yet another object of the embodiments herein is to provide an automated apparatus and method to help the pathologist to navigate to accurate and relevant zones in the specimen.

Yet another object of the embodiments herein is to harvest a maximum number of nodes.

Yet another object of the embodiments herein is to reduce a time taken for grossing process.

Yet another object of the embodiments herein is to provide an automated apparatus and method with a robotic arm, which has three dimensional blades for precise detection and dissection of the specimen of cubes.

Yet another object of the embodiments herein is to provide an automated apparatus and method for processing tissue before performing an automated slide review.

Yet another object of the embodiments herein is o provide an automated apparatus and method for gross processing of tissue with the help of robotics and artificial intelligence.

Yet another object of the embodiments herein is to provide an automated apparatus and method for gross processing of tissue in an enclosed atmosphere to prevent an exposure of pathologist to formalin and risk of infections and accidental injuries during "grossing" process.

Yet another object of the embodiments herein is to provide an automated apparatus and method for gross processing of tissue with a unique way of capturing and integrating the image coupled with transferring the data uniquely to robot to perform tissue grossing process.

Yet another object of the embodiments herein is to provide an automated apparatus and method for gross processing of tissue with an image analysis application and techniques that are applied to objectivize the subjective pathologist reading in a reproducible manner at a stage when a labeled specimen enters grossing-in.

Yet another object of the embodiments herein is to provide an automated apparatus and method for gross processing of tissue to perform 3 dimensional mapping and analysis of the images of the armor tissue, normal tissue, necrotic tissue, and margins with the help of the Image mining algorithms.

Yet another object of the embodiments herein is to provide an automated apparatus and method for gross processing, which is involved only in slicing and block preparation called Grossing).

Yet another object of the embodiments herein is to provide an ultrasound cleaning mechanism built-in in the automated apparatus and method for gross processing of tissue, to keep the instruments clean for a sequential processing.

Yet another object of the embodiments herein is to provide aa automated apparatus for gross processing with a box like structure having a lock-in mechanism thereby enabling a cleaning of all parts effectively and efficiently.

Yet another object of the embodiments herein is to provide an automated apparatus for gross processing having Classification (supervised learning) algorithms/models, and Digital pathology for collaboration.

Yet another object of the embodiments herein is to provide an automated apparatus for gross processing in which a data mining and analytics are carried out at server level.

Yet another object of the embodiments herein is to provide an automated apparatus and method for gross processing in a safe manner to reduce the risk accidental infection to pathologist/technicians during grossing.

Yet another object of the embodiments herein is to provide an automated apparatus and method for gross processing in a safe manner to reduce skin and eye infections due to exposure to formalin.

Yet another object of the embodiments herein is to provide an automated apparatus and method for significantly increasing an accuracy in slicing of the specimen and preserving the integrity of gross specimen.

Yet another object of the embodiments herein is to provide an automated grossing apparatus and method to avoid a lot of problems in grossing like wrong depth during splicing (errors due to inability in understanding a resistivity and hardness of the specimen).

Yet another object of the embodiments herein is to provide an automated grossing apparatus and method to increases an ability to reach deep areas such as areas close to vessels, deep lungs, intramural tumors etc. which are otherwise difficult to reach.

Yet another object of the embodiments herein is to provide an automated grossing apparatus and method integrated with analytic engine, robotic arm, ultrasound mechanism and mobile computing technology.

Yet another objective of the embodiments herein is to provide a system and method for enabling additional reinforcement of the measurements by the indirect measurement techniques like USG, X-Rays, NMR imaging tools for accurate and automated interpretation of gross-examination.

Yet another objective of the embodiments herein is to automate the process of gross-examination by employing a combination of a plurality of technologies such as robotics, analytics, ultrasound, mobile computing etc.

Yet another objective of the embodiments herein is to automate the process of gross-examination by enabling storage of information pertaining to gross-examination on an external server.

Yet another objective of the embodiments herein is to automate the process of gross-examination through machine learning algorithms and methodologies.

Yet another objective of the embodiments herein is to provide a system for evaluating the grossed specimen with help of Imaging (acquired from Ultrasound/X ray/MRI or approved modalities by medical bodies) superimposed with pictorial images of the same taken by conventional/digital imaging based on a AI based correlation.

Yet another objective of the embodiments herein is to provide a system and method of standardizing the consistency of the tissue on a defined scale for uniform reporting by "robotic arm—with specified material, using defined force and proportionate wedge angle of knife/dissecting instrument".

Yet another objective of he embodiments herein is to provide a system and method for accurate pathological dissection to obtain the samples of ideal and relevant areas for processing with the help of image guided robotic navigation of multidimensional blades/instruments, especially for the margins and depth of suspected tissues.

Yet another objective of the embodiments herein is to provide a system and method for an accurate Lymph dissection (plucking rather than cutting) with the help of imaging for standardized yield and thereby preserving the specimen architecture.

Yet another objective of the embodiments herein is to provide a system which is linked with an Artificial Intelligence engine for classification, probabilistic modeling and advanced image analysis of gross-examination of tissues, is provided.

Yet another objective of the embodiments herein is to provide a system and method fix creating analytical models that are specific and customized to each type of specimen being handled.

Yet another objective of the embodiments herein is to provide a system and method for accurate pathological dissection comprising processes such as automated image analysis, remote viewing, pathologists' collaboration and feedback loop, standard image segmentation, storage retrieval etc. which are included in the system as a part of the integrated applications.

These and other objects and advantages of the embodiments herein will become readily apparent from the following detailed description taken in conjunction with the accompanying drawings.

SUMMARY

The various embodiments herein provide system and method for an automated apparatus for the gross examination of tissue sample.

According to one embodiment herein, an automated apparatus for the gross examination of tissue sample is provided. The apparatus is of cubicle or rectangular shape comprising a bed where the specimen is placed, an ultrasound equipment mounted under the bed, camera mounted on 3-D movable arm for accurately capturing the image for the detailing of the specimen and a robotic arm capable of moving in X-axis, Y-axis and Z-axis, a plurality of surgical blades housed in the cubicle box and mounted in the robotic arm. A 3D movable camera captures the details of the specimen to be grossed, similar to a naked eye but with objectification. The ultrasound technology is used to accurately understand the specimen, size and dimensions of a tumor that is studied. The ultrasound equipment also assists in the automation of the process of cutting the specimen. The surgical blades receive ultrasound output and accurately slice the specimen for further analysis.

According to one embodiment herein, a precision instrument, which is linked with an Artificial intelligence engine for classification, probabilistic modeling and advanced image analysis of gross-examination of tissues, is provided. All these are analytical models that are specific and customized to each type of specimen being handled. Processes such as automated image analysis, remote viewing, pathologists' collaboration, standard image segmentation, storage retrieval etc. are included in the system as a part of the integrated applications.

According to one embodiment herein, an apparatus for enabling automated gross-examination of tissues is provided. The apparatus comprises stainless steel bed for placing the tissue sample, cubes of multiple sizes to act as the base for the bed, mountable ultrasound equipment and retractable robotic blades are provided. The Stainless steel bed is provided with a disposable cover for each specimen. The Bed is configured to slide out and when bed is outside, to avoid accidental injury. The blades inside robotic are retracted inside. Only on completion of ultrasound and confirmation by pathologist the blades are extended out of the robotic arm.

According to one embodiment herein, the apparatus is provided with a built-in ultrasound cleaning mechanism to keep the instruments clean for a sequential processing.

According to one embodiment herein, the box is formed or fabricated in three sizes of 30/60/90 sqcm with bed arranged at a ⅔rd height from the base. The bed is provided on top with a piezoelectric glass mounted with the ultrasound equipment. The bed is connected with a motor for rotating the bed for assisting the dissection process of grossing-in and enable imaging process. The box has a modular design with lock-in mechanisms to ensure that all the parts are opened and cleaned manually by an operator or a lab technician with a minimal training. The ultrasound equipment is arranged or configured to cover an entire surface area on top of the bed. Alternatively the ultrasound equipment is arranged as an array for covering specimen per sqmm.

According to one embodiment herein, the robotic arm is mounted with medical grade surgical blades (like scalpel) with a retractable mechanism for safety. The 3 blades are configured to cover X-Y-Z axes As soon as the specimen is sliced, the blades are cleaned with an ultrasound mechanism. The equipment is provided with an automatic cleaning facility arranged inside and is cleaned later manually. An output of ultrasound is input to robotic arm, based on the command issued from the server after the analysis by the pathologist and analytics from server to cut and slice the sample for analysis. The output of ultrasound is input to robotic arm, for precise detection and dissection of specimen into cubes of preset sizes using the medical grade blades. The cubes are transferred with help of robotic arm into automatic wax block for preparation, which are then subjected to analysis.

According to one embodiment herein, any analytics on AI and Machine learning is carried out in the server and the results are communicated the apparatus from the server. A plurality of classification (supervised learning) algorithms/models, and Digital pathology for collaboration are employed in the analysis of the samples.

According to one embodiment herein, the apparatus is configured to perform automatic process of grossing of tissues by integrating the technologies of data mining, analytics, robotics, ultrasound and mobile computing.

According to one embodiment herein, the apparatus is configured to storage data/information related to gross-examination of tissue samples on an external server.

According to one embodiment herein, a method is provided with the steps involved in a preliminary identification and recording information about a gross-examination sample. The method comprises the following steps: Identification of the nomenclature and taxonomy of a specimen; Placement of the specimen is on the ultrasound bed laterally depending on the size of the specimen; The specimen is stabilized with a robotic arm and the measurements of the specimen are captured by ultrasound technique; The specimen is video graphed and contour shape is recorded; and, Measurements are analyzed by pathologists; when the pathologists approve the measurements, the measurements and shape of the specimen are recorded in the database. When the pathologists do not approve the measurements, the pathologist modifies the measurements and the measurements and shape of the specimen are recorded in the database.

According to one embodiment herein, a method is provided with the steps involved in an image analysis of a gross-examination sample. The method comprises the folk wino steps: The analysis of the specimen is carried out by the ultrasound waves and the waves are converted into co-ordinates by a computer algorithm; An image is captured by a piezoelectric device with the help of ultrasound waves and the image is sent to the image analysis algorithm for further analysis; The total size of the tumor versus the total size of the specimen is identified from the sonic imaging and the location of the tumor is identified with respect to its boundaries from left to right; The size of the tumor as per general slicing is also captured and stored for further use and the lymph nodes are counted from the image analysis and are mapped to the co-ordinates and nodal dissection takes place; and, The specimen is sliced from left to right while enabling more slicing at the boundaries of the tumor and while slicing the tumor, the grittiness and the texture of the tumor are captured.

According to one embodiment herein, a method is provided with the steps involved in generating an analysis report of a gross-examination sample after conducting an image analysis on the sample, according to one embodiment herein. The method comprises the following steps: Once the slicing is done the robotic arm disengages and the tumor is held for further clinical purposes; The tumor is then dissected to obtain a block of tumor by the robotic arm as per the grossing principles; A predefined full report is generated with all the necessary information; and, The report and the block are sent for further clinical purposes.

According to one embodiment herein, a system is provided to enable texture and consistency analysis and reporting of a sample. The system comprises automated/manual robotic arm with 3D control, a module with pressure/time/power gradient control coupled with movement measurement technology and a module for measurement of resistance/movement traversed with outputs based on programmed calculator for consistency. The embodiment also comprises a module with a standardized scale with a validated score system to objectively document the consistency and texture, that is reported automatically with a pathologist/a technical expert interface to minimize false negatives and errors. The embodiment also comprises an artificial intelligence module that comprises: input capturing in terms of force vs. movement vs. time vs. texture and coupling with graded output for dissecting to robotic arm; data integration with image [Visual/optical] vs. Scan [electromagnetic/piezoelectric/texture/tensile and other properties; artificial intelligence based algorithm for the forward. and backward integration; and, automated typing into the pre-formatted testing taking inputs specific to organ.

According to one embodiment herein, a system is provided to enable sensor-blade technology in the robotic arm in the apparatus. The system comprises a module with an intact tissue sliced and the scanner integrated with blade, a module with a feedback loop from the technical interface/historical control/machine learning controls the dissecting pressure and distance to be traversed, a module with a pressure too low that undercuts and be augmented by positive feedback loop, a module with a pressure too high that overcuts and be inhibited by negative feedback loop; and a module with an accurate dissection with texture/consistency oriented outputs, which are objective and quantifiable.

According to one embodiment herein, a system is provided to enable Lymph-node plucking with the present apparatus. The system comprises a Lymph-node sample, a module with a 3D controlled human interface enabled arm having inputs from the Imaging and Scanning integrated with pathologist inputs, a module with a plurality of outputs to a plucker/rotator blade [not slicing, which is unique] that plucks without damaging the surrounding tissues, a module with image based mapping of the spherico ovaoidal structures, having high probabilistic chances of being Lymph nodes and coordinates to be sent to the robotic arm and a final feedback loop coupled with artificial intelligence makes the prediction better with machine learning and technical interface for better nodal yield. The plucking/circular cutting minimizes damage to surroundings of the sample.

According to one embodiment herein, a system is provided to enable a development of predicting modeling tool for malignant potential based on the final HPE to integrate for a routine imaging with artificial intelligence. The system comprises a module with grossing results coupled with final HPE from the master database/computer, which are specific to the tissues and organ, a module with results of imaging/scanning from the database corresponding to the specimen, a module comprising artificial intelligence based algorithm for machine learning to predict the characters unique for malignant vs. benign tissues and final software that predicts malignant potential at the scanning level itself in the live organisms/humans.

According to one embodiment herein, a system is provided for transferring information from an ultrasonic generator to correlating software for pathology image. The system comprises a cloud module with data from USG and final pathology from automated grossing machine, a module for analysis of textures as measured with resistivity index, a module for analysis of image textures from camera and ultrasound, a module to send for the artificial algorithm for correlation to HPE, a module to send for artificial intelligence platform for pattern recognition and validated outputs and an image-pathological correlating software.

According to an embodiment herein, a system is configured to evaluate the grossed specimen by superimposing the images acquired from Ultrasound/X ray/MRI or approved modalities by medical bodies with pictorial images of the same taken by conventional/digital imaging based on a AI based correlation.

According to an embodiment herein, a system is configured to standardize the consistency of the tissue on a defined scale for uniform reporting by "robotic arm—with specified material, using defined force and proportionate wedge angle of knife/dissecting instrument".

According to an embodiment herein, a system is configured to perform an accurate pathological dissection to obtain the samples of ideal and relevant areas for processing with the help of image guided robotic navigation of multidimensional blades/instruments, especially for the margins and depth of suspected tissues.

According to an embodiment herein, a system is configured to carry out an accurate Lymphnodal dissection (plucking rather than cutting) with the help of imaging for standardized yield and thereby preserving the specimen architecture.

According to an embodiment herein, a system is linked with an Artificial Intelligence engine for classification, probabilistic modeling and advanced image analysis of gross-examination of tissues.

According to an embodiment herein, the system is further configured to create analytical models that are specific and customized to each type of specimen being handled.

According to an embodiment herein, the system is further configured to perform accurate pathological dissection comprising processes such as automated image analysis, remote viewing, pathologists' collaboration and feedback loop, standard image segmentation, storage retrieval etc. which are included m the system as a part of the integrated applications.

According to an embodiment herein, a method further comprises evaluating the grossed specimen by superimposing the images acquired from Ultrasound/X ray/MRI or approved modalities by medical bodies with pictorial images of the same taken by conventional/digital imaging based on a AI based correlation.

According to art embodiment herein, the method further comprises the steps of standardizing the consistency of the tissue on a defined scale for uniform reporting by "robotic arm—with specified material, using defined force and proportionate wedge angle of knife/dissecting instrument".

According to an embodiment herein, the method further comprises the steps of performing an accurate pathological dissection to obtain the samples of ideal and relevant areas for processing with the help of image guided robotic navigation of multidimensional blades/instruments, especially for the margins and depth of suspected tissues.

According to an embodiment herein, the method further comprises the steps of performing an accurate Lymphnodal dissection (plucking rather than cutting) with the help of imaging for standardized yield and thereby preserving the specimen architecture.

According to an embodiment herein, the method further comprises the steps for performing a classification, a probabilistic modeling and an advanced image analysis of gross-examination of tissues by using an Artificial Intelligence engine.

According to an embodiment herein, the method further comprises the steps of creating the analytical models that are specific and customized to each type of specimen being handled.

According to an embodiment herein, the method further comprises the steps of performing an accurate pathological dissection comprising processes such as automated image analysis, remote viewing, pathologists' collaboration and feedback loop, standard image segmentation, storage retrieval etc. which are included in the system as a part of the integrated applications.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof and the embodiments herein include all such modifications.

BRIEF DESCRIPTION OF THE DRAWINGS

The other objects, features and advantages will occur to those skilled in the art from the following description of the preferred embodiment and the accompanying drawings in which.

Figure 1:
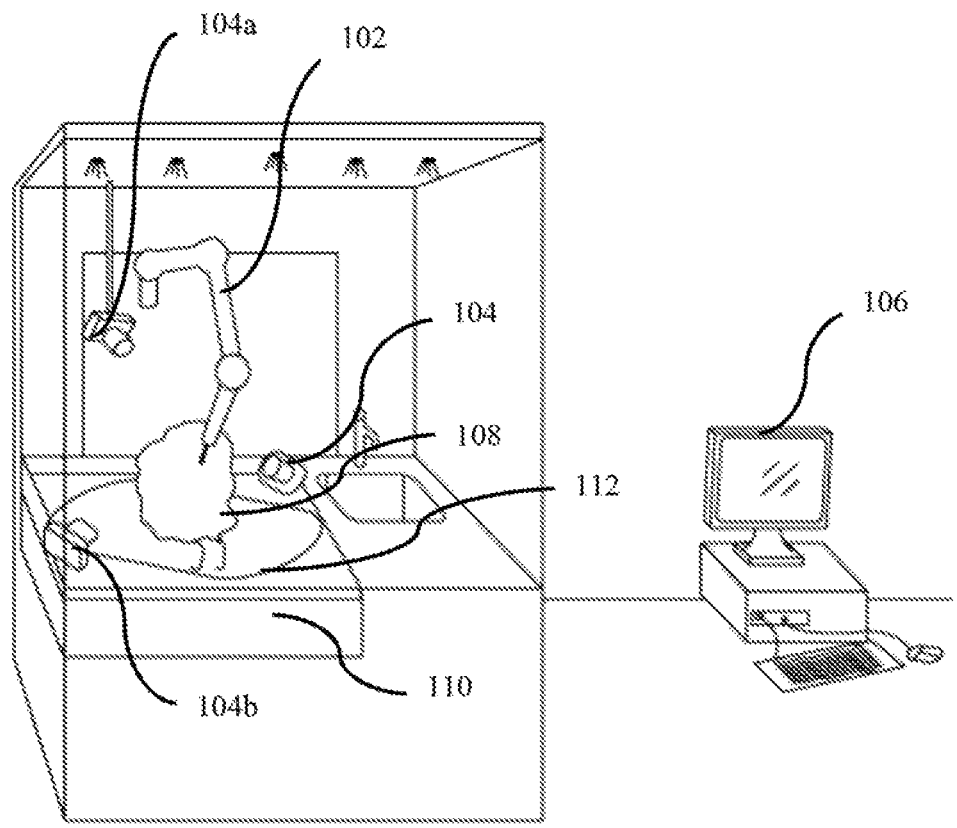
FIG. 1 illustrates a perspective view of an apparatus for automatic gross-examination of tissue samples, according to one embodiment herein.

Although the specific features herein are shown in some drawings and not in others. This is done for convenience only as each feature may be combined with any or all of the other features in accordance Faith the embodiments herein.

DETAILED DESCRIPTION OF THE INVENTION

In the following detailed description, a reference is made to the accompanying drawings that form a part hereof, and in which the specific embodiments that may be practiced is shown by way of illustration. These embodiments are described in sufficient detail to enable those skilled in the art to practice the embodiments and it is to be understood that other changes may be made without departing from the scope of the embodiments. The following detailed description is therefore not to be taken in a limiting sense.

The various embodiments herein provide system and method for an automated apparatus for the gross examination of tissue sample.

According to one embodiment herein, an automated apparatus for the gross examination of tissue sample is provided. The apparatus is of cubicle or rectangular shape or other suitable shape comprising a bed where the specimen is placed, an ultrasound equipment mounted under the bed, camera mounted on a 3D movable arm for accurately capturing the image for the detailing of the specimen and a robotic arm capable of moving in X-axis, Y-axis and Z-axis, a plurality of surgical blades housed in the cubicle box and mounted in the robotic arm. A 3D movable camera captures the details of the specimen to be grossed, similar to naked eye but with objectification. The ultrasound technology is used to accurately understand the specimen, size and dimensions of a tumor that is studied. The ultrasound equipment also assists in the automation of the process of cutting the specimen. The surgical blades receive the output from the ultrasound equipment or other imaging devices to accurately slice the specimen for further analysis.

According to one embodiment herein, a precision instrument, which is linked with an Artificial Intelligence engine for classification, probabilistic modeling and advanced image analysis of gross-examination of tissues, is provided. All these are analytical models that are specific and customized to each type of specimen being handled. Processes such as automated image analysis, remote viewing, pathologists' collaboration, standard image segmentation, storage retrieval etc. are included in the system as a part of the integrated applications.

According to one embodiment herein, an apparatus for enabling automated gross-examination of tissues is provided. The apparatus comprises stainless steel bed for placing the tissue sample, cubes of multiple sizes to act as the base for the bed, mountable ultrasound equipment and retractable robotic blades are provided. The piezo-electric compatible bed fixed on stainless steel based motor enabled plate is provided with a disposable cover for each specimen. The Bed is configured to slide out and when bed is outside, to avoid accidental injury. The blades inside robotic are retracted inside. Only on completion of ultrasound and confirmation by pathologist the blades are extended out of the robotic arm.

According to one embodiment herein, the apparatus is provided with a built-in ultrasound cleaning mechanism to keep the instruments clean for a sequential processing.

According to one embodiment herein, the box is formed or fabricated in three sizes of 30/60/90 sqcm with bed arranged at a ⅔rd height from the base. The bed is provided on top with a piezoelectric glass mounted with the ultrasound equipment. The bed is connected to a motor for rotating the bed for assisting the dissection process of grossing-in and imaging operations. The box has a modular design with lock-in mechanisms to ensure that all the pans are opened and cleaned manually by an operator or a lab technician with a minimal training. The ultrasound equipment is arranged or configured to cover an entire surface area on top of the bed. Alternatively the ultrasound equipment is arranged as an array for covering specimen per sqmm.

According to one embodiment herein, the robotic arm is mounted with medical grade surgical blades (like scalpel) with a retractable mechanism for safety. The 3 blades are configured to cover X-Y-Z axes As soon as the specimen is sliced, the blades are cleaned with an ultrasound mechanism. The equipment is provided with an automatic cleaning facility arranged inside and is cleaned later manually. An output of ultrasound is input to robotic arm, based on the command issued from the server after the analysis by the pathologist and analytics from server to cut and slice the sample for analysis. The output of ultrasound is input to robotic arm, for precise detection and dissection of specimen into cubes of preset sizes using the medical grade blades. The cubes are transferred with help of robotic arm into automatic wax block for preparation, which are then subjected to analysis.

According to one embodiment herein, any analytics on AI and Machine learning is carried out in the server and the results are communicated the apparatus from the server. A plurality of classification (supervised learning) algorithms/ models, and Digital pathology for collaboration are employed in the analysis of the samples.

According to one embodiment herein, the apparatus is configured to perform automatic process of grossing of tissues by integrating the technologies of data mining, analytics, robotics, ultrasound and mobile computing.

According to one embodiment herein, the apparatus is configured to storage data/information related to gross-examination of tissue samples on an external server.

According to an embodiment herein, a system is configured to evaluate the grossed specimen by superimposing the images acquired from Ultrasound/X ray/MRI or approved modalities by medical bodies with pictorial images of the same taken by conventional/digital imaging based on an AI based correlation.

According to an embodiment herein, a system is configured to standardize the consistency of the tissue on a defined scale for uniform reporting by "robotic arm—with specified material, using defined force and proportionate wedge angle of knife/dissecting instrument".

According to an embodiment herein, a system is configured to perform an accurate pathological dissection to obtain the samples of ideal and relevant areas for processing with the help of image guided robotic navigation of multidimensional blades/instruments, especially for the margins and depth of suspected tissues.

According to an embodiment herein, a system is configured to carry out an accurate Lymphnodal dissection (plucking rather than cutting) with the help of imaging for standardized yield and thereby preserving the specimen architecture.

According to an embodiment herein, a system is linked with an Artificial Intelligence engine for classification, probabilistic modeling and advanced image analysis of gross-examination of tissues.

According to an embodiment herein, the system is further configured to create analytical models that are specific and customized to each type of specimen being handled.

According to an embodiment herein, the system is further configured to perform accurate pathological dissection comprising processes such as automated image analysis, remote viewing, pathologists' collaboration and feedback loop, standard image segmentation, storage retrieval etc. which are included in the system as a part of the integrated applications.

According to an embodiment herein, a method further comprises evaluating the grossed specimen by superimposing the images acquired from Ultrasound/X ray/MRI or approved modalities by medical bodies with pictorial images of the same taken by conventional/digital imaging based on a AI based correlation.

According to an embodiment herein, the method further comprises the steps of standardizing the consistency of tie tissue on a defined scale for uniform reporting by "robotic arm—with specified material, using defined force and proportionate wedge angle of knife/dissecting instrument".

According to an embodiment herein, the method further comprises the steps of performing an accurate pathological dissection to obtain the samples of ideal and relevant areas fur processing with the help of image guided robotic navigation of multidimensional blades/instruments, especially for the margins and depth of suspected tissues.

According to an embodiment herein, the method further comprises the steps of performing an accurate Lymphnodal dissection (plucking rather than cutting) with the help of imaging for standardized yield and thereby preserving the specimen architecture.

According to an embodiment herein, the method further comprises the steps for performing a classification, a probabilistic modeling and an advanced image analysis of gross-examination of tissues by using an Artificial Intelligence engine.

According to an embodiment herein, the method further comprises the steps of creating the analytical models that are specific and customized to each type of specimen being handled.

According to an embodiment herein, the method further comprises the steps of performing an accurate pathological dissection comprising processes such as automated image analysis, remote viewing, pathologists' collaboration and feedback loop, standard image segmentation, storage retrieval etc. which are included in the system as a part of the integrated applications.

FIG. 1 illustrates a perspective view of an apparatus for automatic gross-examination of tissue samples, according to an embodiment herein. With respect to FIG. 1, an automated apparatus for the gross examination of tissue sample is provided. The apparatus is of cubicle shaped box comprising a bed 110 where the specimen 108 is placed. An ultrasound equipment is mounted on top of the bed 110 and a robotic arm 102 capable of moving in X-axis, Y-axis and Z-axis is fixed to the top of the box. A plurality of surgical blades is mounted in the robotic arm 102. The blades are configured to extend out during a dissection process and are retracted back inside the arm 102 when not in use. The ultrasound technology is used to accurately understand/detect the specimen, size and dimensions of a tumor that is studied. The ultrasound equipment also automates the process of cutting the specimen 108. The surgical blades receive ultrasound output and accurately slice the specimen for further analysis. A camera 104a, is mounted on 3 D movable arm for accurate capturing of the image for the detailing of the specimen. A plurality of 3D movable cameras 104,104a, 104b is provided to capture the details of the specimen to be grossed, similar to naked eye but with objectification.

According to one embodiment herein, a precision instrument, which is linked with an Artificial Intelligence engine for classification, probabilistic modeling and advanced image analysis of gross-examination of tissues, is provided. All these are analytical models that are specific and customized to each type of specimen being handled. Processes such as automated image analysis, remote viewing, pathologists' collaboration, standard image segmentation, storage retrieval etc. are included in the system as a part of the integrated applications.

According to one embodiment herein, the apparatus comprises stainless steel bed 110 for placing the tissue sample. The bed is mounted with a piezo electric glass 112 on top. A ultrasound equipment is mounted on the bed. The retractable robotic blades are provided. The Stainless steel bed 110 is provided with a disposable cover for each specimen. The Bed 110 is configured to slide out and when bed is outside, to avoid accidental injury. The blades are retracted inside robotic arm, when not in use. Only on completion of ultrasound and confirmation. by pathologist, the blades are extended out of the robotic arm.

According to one embodiment herein, the apparatus is provided with a built-in ultrasound cleaning mechanism to keep the instruments clean for a sequential processing.

According to one embodiment herein, the box is formed or fabricated in three sizes of 30/60/90 sqcm with bed arranged at a ⅔rd height from the base. The box has a modular design with lock-in mechanisms to ensure that all the parts are opened and cleaned manually by an operator or a lab technician with a minimal training. The ultrasound equipment is arranged or configured to cover an entire surface area on top of the bed. Alternatively the ultrasound equipment is arranged as an array for covering specimen per sqmm.

According to one embodiment herein, the robotic arm is mounted 102 with medical grade surgical blades (like scalpel) with a retractable mechanism for safety. The 3 blades are configured to cover X-Y-Z axes As soon as the specimen is sliced, the blades are cleaned with an ultrasound mechanism. The equipment is provided with an automatic cleaning facility arranged inside and is cleaned later manually. An output of ultrasound is input to robotic arm, based on the command issued from the server after the analysis by the pathologist and analytics from server to cut and slice the sample for analysis. The output of ultrasound is input to robotic arm, for precise detection and dissection of specimen into cubes of preset sizes using the medical grade blades. The cubes are transferred with help of robotic arm into automatic wax block for preparation, which are then subjected to analysis.

According to one embodiment herein, any analytics on AI and Machine learning is carried out in the server 106 and the results are communicated the apparatus from the server 106. A plurality of classification (supervised learning) algorithms/models, and Digital pathology for collaboration are employed in the analysis of the samples.

Figure 2:
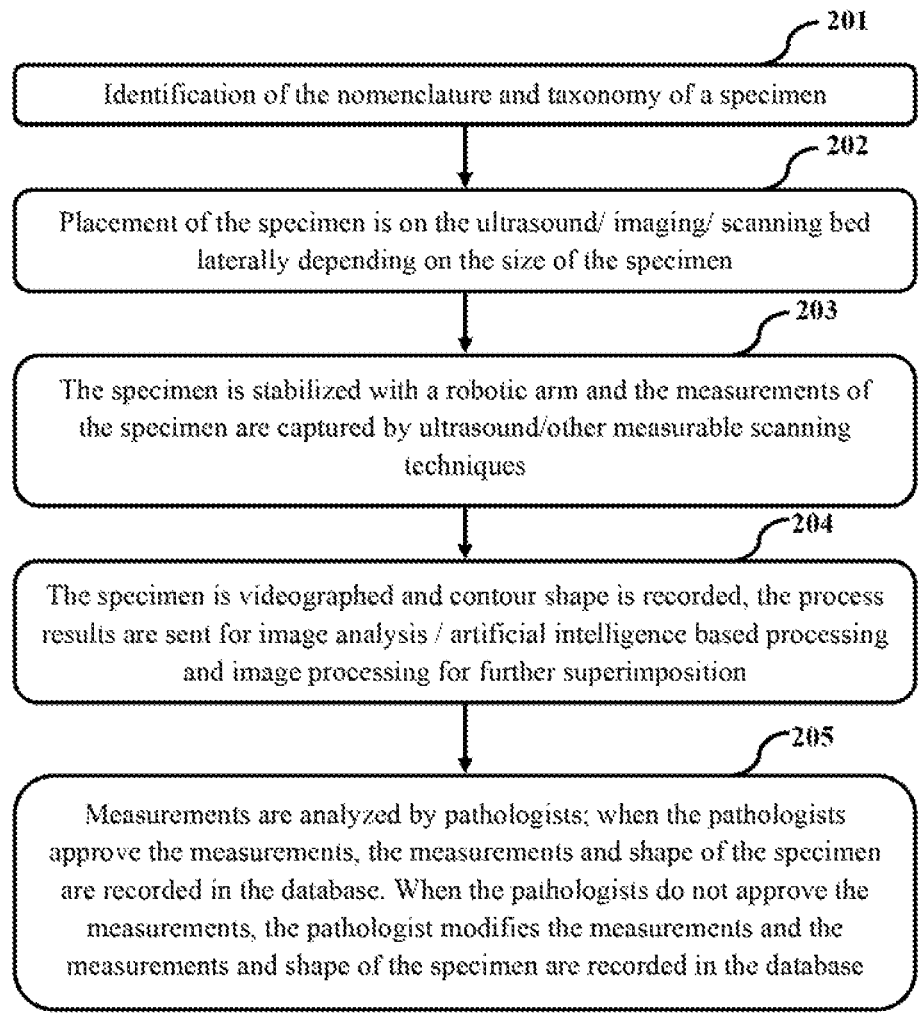
FIG. 2 illustrates a flow diagram that provides the steps involved in a preliminary identification and recording information about a gross-examination sample, according to one embodiment herein.

FIG. 2 illustrates a flow diagram that provides the steps involved in a preliminary identification and recording information about a gross-examination sample, according to one embodiment herein. The method comprises the following steps: Identification. of the nomenclature and taxonomy of a specimen (201); Placement of the specimen is on the ultrasound bed laterally depending on the size of the specimen (202). The specimen is stabilized with a robotic arm and the measurements of the specimen are captured by ultrasound technique (203); The specimen is videographed and contour shape is recorded (204); and, Measurements are analyzed by pathologists; when the pathologists approve the measurements, the measurements and shape of the specimen are recorded in the database. When the pathologists do not approve the measurements, the pathologist modifies the measurements and the measurements and shape of the specimen are recorded in the database (205).

Figure 3:
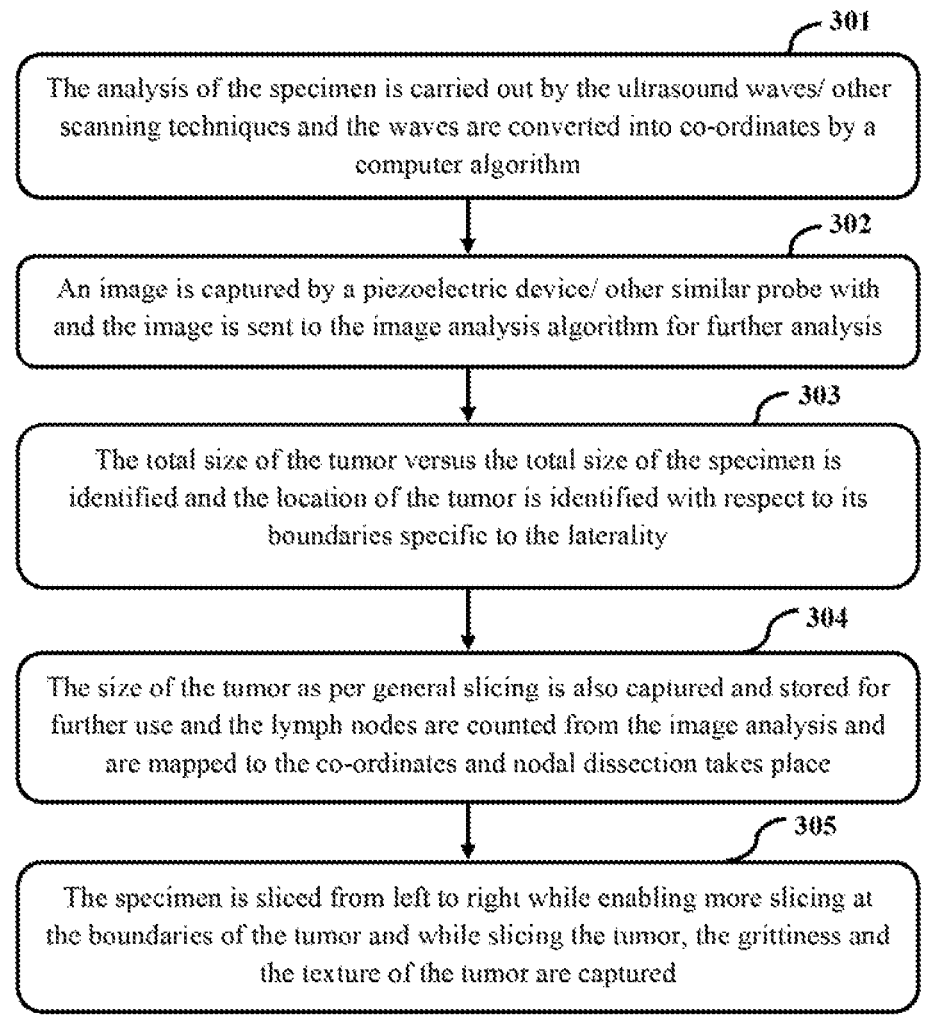
FIG. 3 illustrates a flow diagram that provides the steps involved in an image analysis of a gross-examination sample, according to one embodiment herein.

FIG. 3 illustrates a flow diagram that provides the steps involved in an image analysis of a gross-examination sample, according to one embodiment herein. The method comprises the following steps: The analysis of the specimen is carried out by the ultrasound waves and the waves are converted into co-ordinates by a computer algorithm (301); An image is captured by a piezoelectric device with the help of ultrasound waves and the image is sent to the image analysis algorithm for further analysis (302); The total size of the tumor versus the total size of the specimen is identified from the sonic imaging and the location of the tumor is identified with respect to its boundaries from left to right (303); The size of the tumor as per general slicing is also captured and stored for further use and the lymph nodes are counted from the image analysis and are mapped to the co-ordinates and nodal dissection takes place (304); and, The specimen is sliced from left to right while enabling more slicing at the boundaries of the tumor and while slicing the tumor, the grittiness and the texture of the tumor are captured (305).

Figure 4:
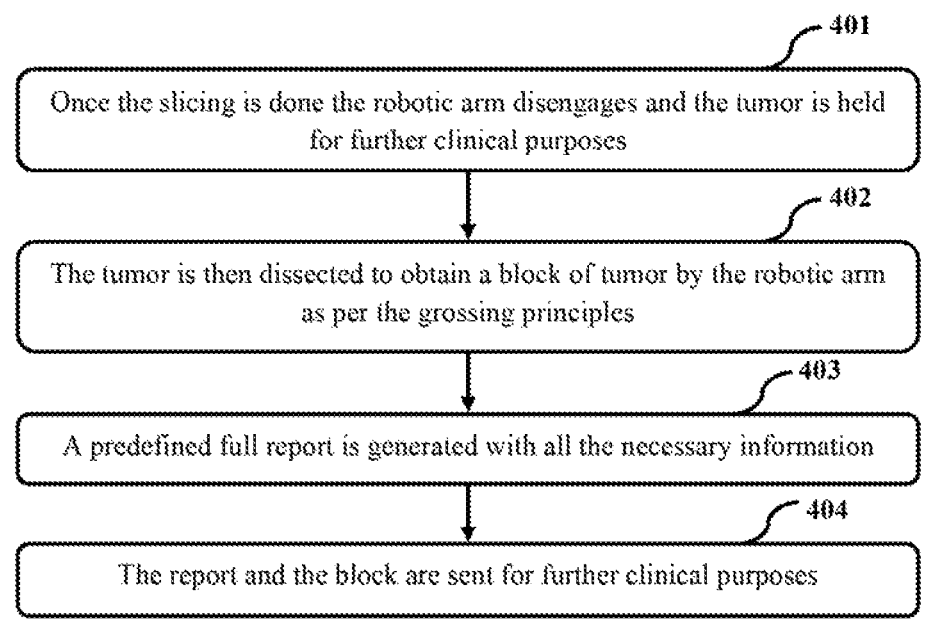
FIG. 4 illustrates a flow diagram that provides the steps involved in generating an analysis report of a gross-examination sample after conducting an image analysis on the sample, according to one embodiment herein.

FIG. 4 illustrates a flow diagram that provides the steps involved in generating an analysis report of a gross-examination sample after conducting an image analysis on the sample, according to one embodiment herein. The method comprises the following steps: Once the slicing is done the robotic arm disengages and the tumor is held for further clinical purposes (401); The tumor is then dissected to obtain a block of tumor by the robotic arm as per the grossing principles (402); A predefined full report is generated with all the necessary information (403); and, The report and the block are sent for further clinical purposes (404).

Figure 5:
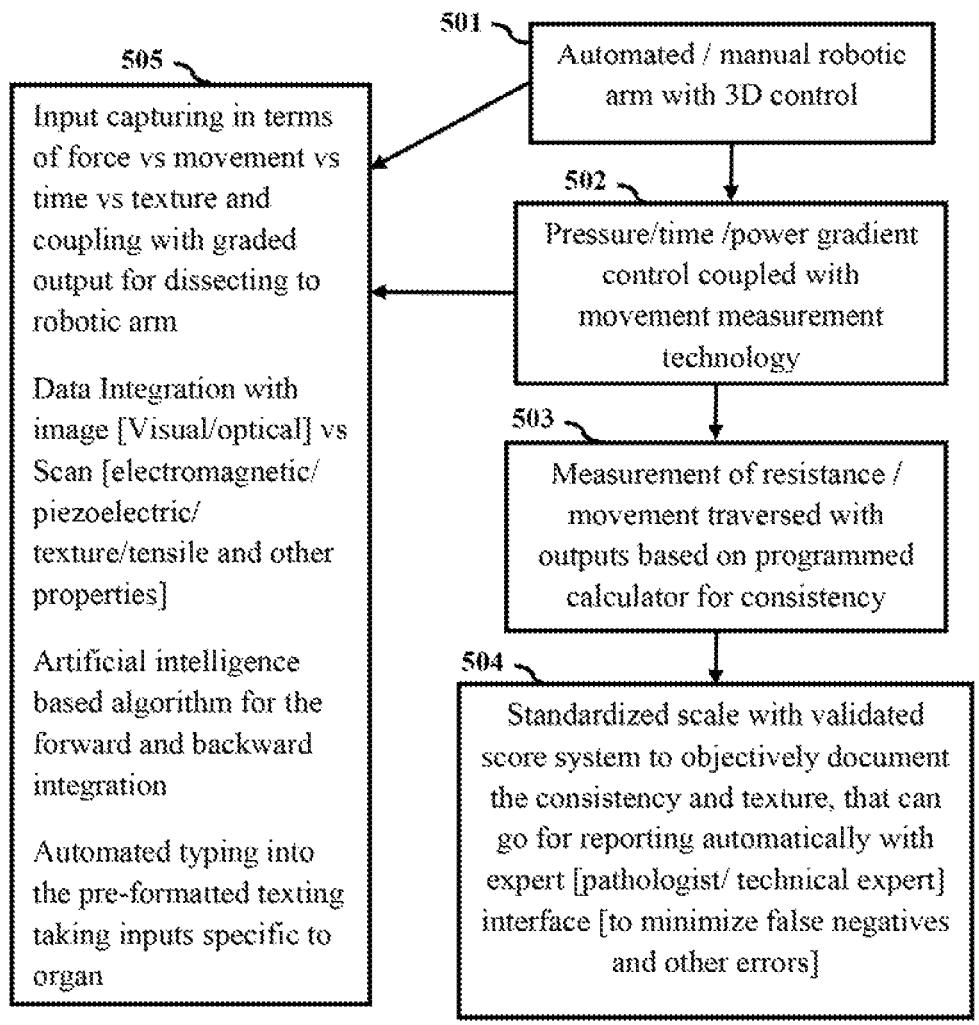
FIG. 5 illustrates a system that enables texture and consistency analysis and reporting of a sample, according to one embodiment herein.

FIG. 5 illustrates a system that enables texture and consistency analysis and reporting of a sample, according to one embodiment herein. The system comprises an automated/manual robotic arm with 3D control 501, a module with pressure/time/power gradient control coupled with movement measurement technology 502 and a module for measurement of resistance/movement traversed with outputs based on programmed calculator for consistency. The embodiment also comprises a module 504 with a standardized scale with a validated score system to objectively document the consistency and texture, that is reported automatically with a pathologist/a technical expert interface to minimize false negatives and errors. The embodiment also comprises an artificial intelligence module 505 that comprises: input capturing in terms of force vs. movement vs. time vs, texture and coupling with graded output for dissecting to robotic arm; data integration with image [Visual/optical] vs. Scan [electromagnetic/piezoelectric/texture/tensile and other properties; artificial intelligence based algorithm for the forward and backward integration; and, automated typing into the pre-formatted texting taking inputs specific to organ.

Figure 6:
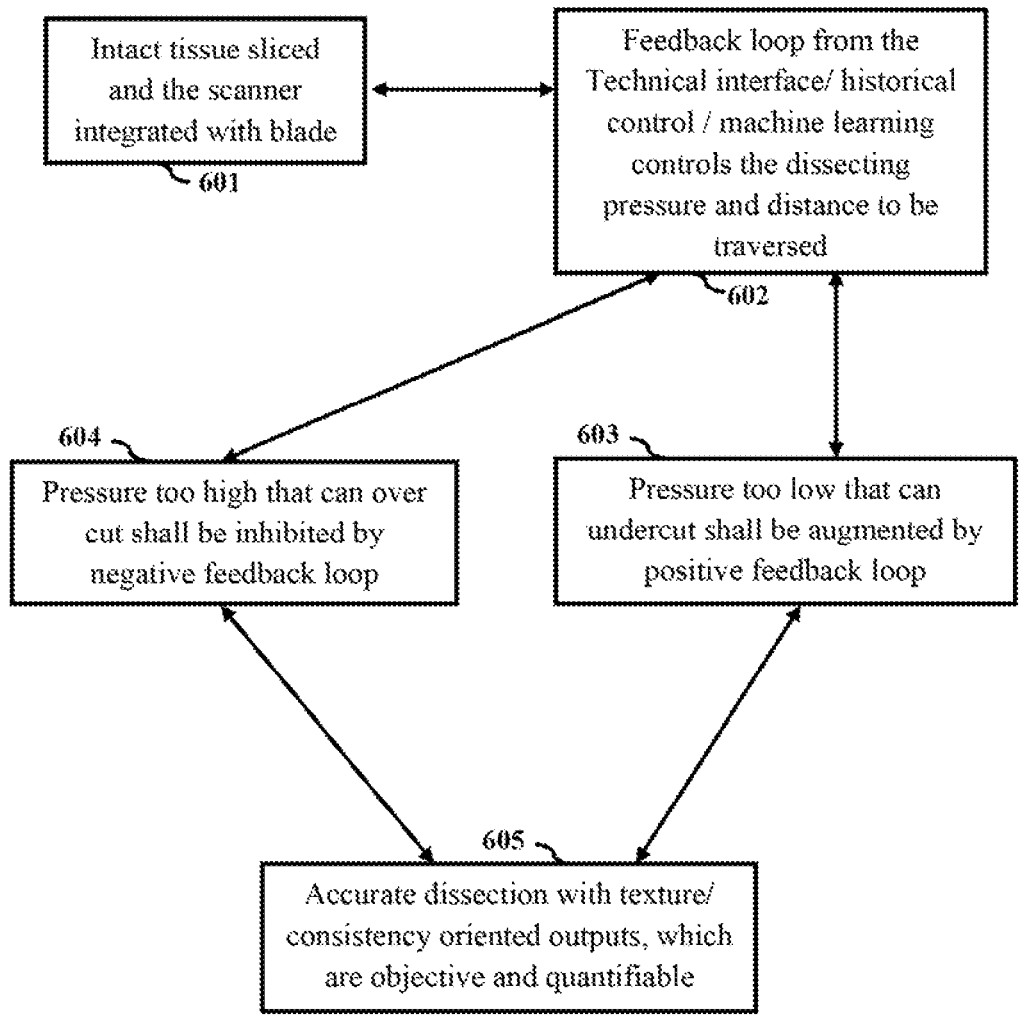
FIG. 6 illustrates a system that enables the sensor-blade technology in the robotic arm in the apparatus, according to one embodiment herein.

FIG. 6 illustrates a system that enables the sensor-blade technology in the robotic arm in the apparatus, according to one embodiment herein. The system comprises a module with an intact tissue sliced and the scanner integrated with blade 601, a module with a feedback loop from the technical interface/historical control/machine learning controls the dissecting pressure and distance to be traversed 602, a module with a pressure too low that undercuts and be augmented by positive feedback loop 603, a module with a pressure too high that overcuts and be inhibited by negative feedback loop 604; and a module with an accurate dissection with texture/consistency oriented outputs, which are objective and quantifiable 605.

Figure 7:
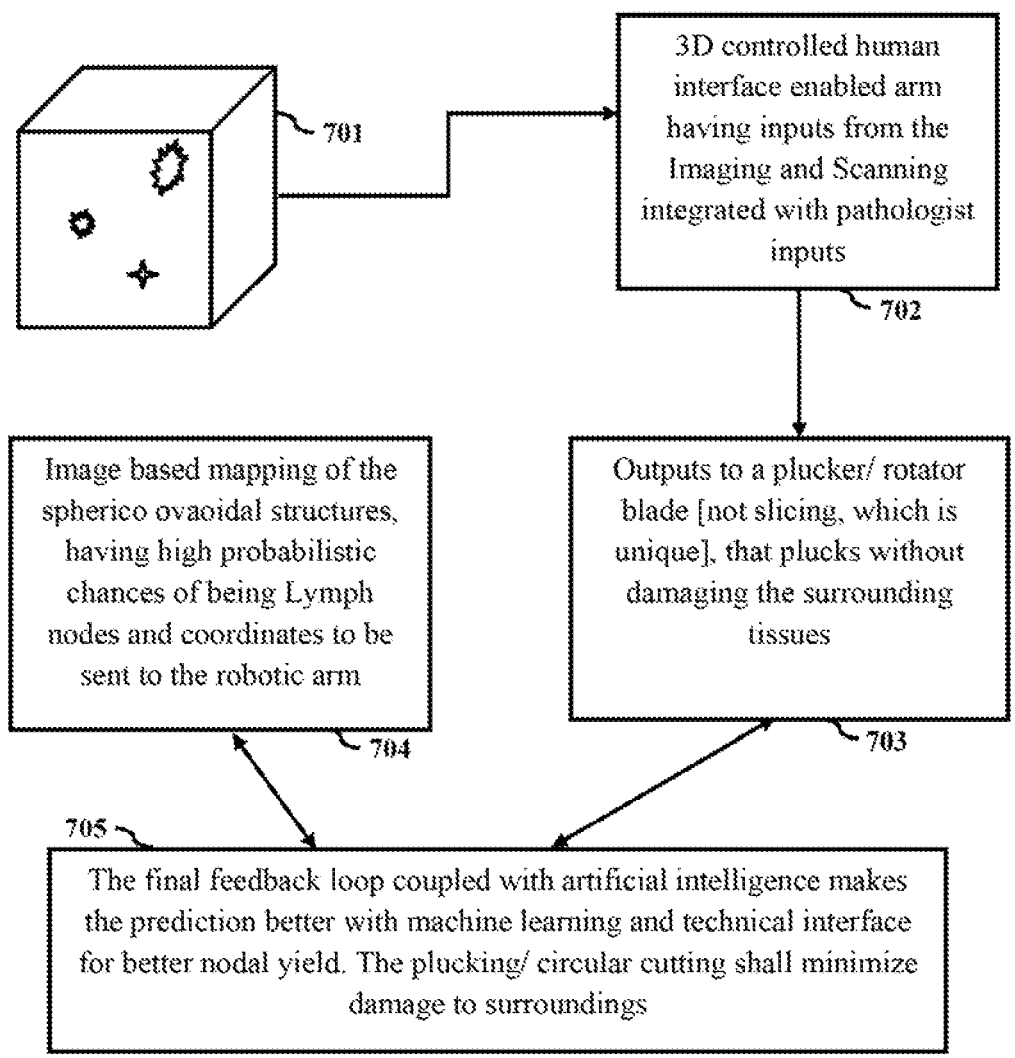
FIG. 7 illustrates a system that enables Lymph-node plucking with present apparatus, according to one embodiment herein.

FIG. 7 illustrates a system that enables Lymph-node plucking with the present apparatus, according to one embodiment herein. The system comprises a Lymph-node sample 701, a module with a 3D controlled human interface enabled arm having inputs from the Imaging and. Scanning integrated with pathologist inputs 702, a module with a plurality of outputs to a plucker/rotator blade [not slicing, which is unique] that plucks without damaging the surrounding tissues 703, a module with image based mapping of the spherico ovaoidal structures, having high probabilistic chances of being Lymph nodes and coordinates to be sent to the robotic arm 704 and a final feedback loop coupled with artificial intelligence makes the prediction better with machine learning and technical interface for better nodal yield 705. The plucking/circular cutting minimizes damage to surroundings of the sample.

Figure 8:
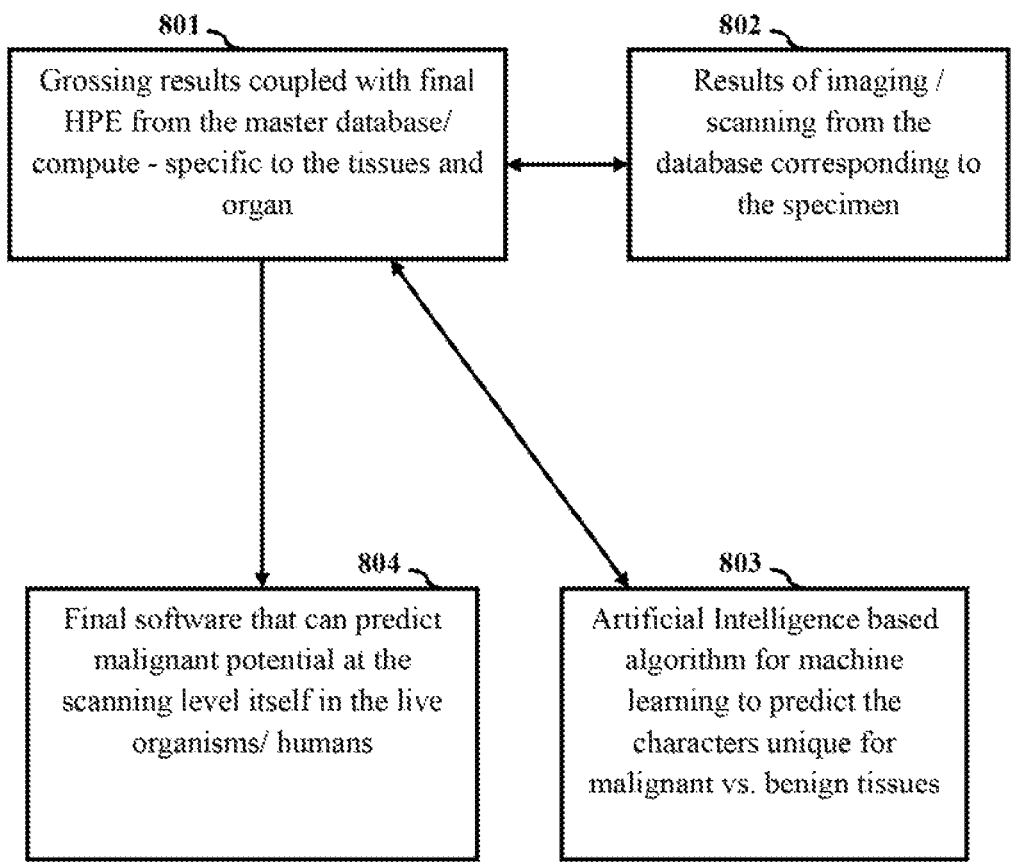
FIG. 8 illustrates a system that enables a development of predicting modeling tool for malignant potential based on the final HPE to integrate for a routine imaging with artificial intelligence, according to one embodiment herein.

FIG. 8 illustrates a system that enables a development of predicting modeling tool for malignant potential based on the final HPE to integrate for a routine imaging with artificial intelligence, according to one embodiment herein. The system comprises a module with grossing results coupled with final HPE from the master database/computer, which are specific to the tissues and organ 801, a module with results of imaging/scanning from the database corresponding to the specimen 802, a module comprising artificial intelligence based algorithm far machine learning to predict the characters unique far malignant vs. benign tissues 803 and final software that predicts malignant potential at the scanning level itself in the live organisms/humans 804.

Figure 9:
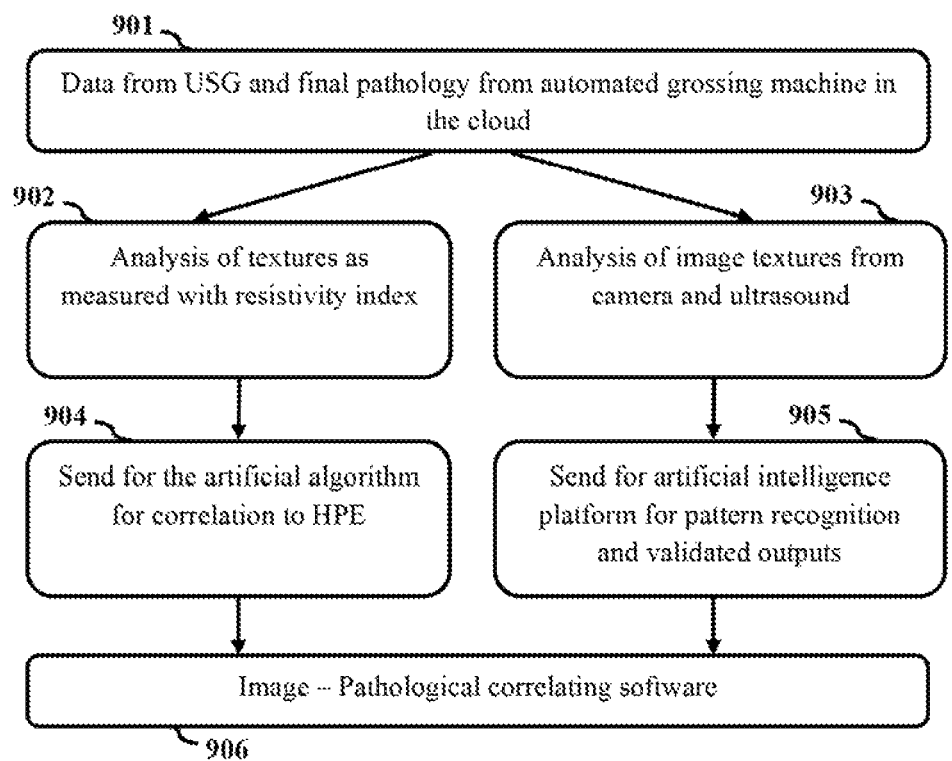
FIG. 9 illustrates a system for transferring information from an ultrasonic generator to correlating software for pathology image, according to one embodiment herein.

FIG. 9 illustrates a system for transferring information from an ultrasonic generator to correlating software for pathology image, according to one embodiment herein. The system comprises a cloud module with data from USG and final pathology from automated grossing machine 901, a module for analysis of textures as measured, with resistivity index 902, a module for analysis of image textures from camera and ultrasound 903, a module to send for the artificial algorithm for correlation to HPE 904, a module to send for artificial intelligence platform for pattern recognition and validated outputs 905 and an image-pathological correlating software.

The foregoing description of the specific embodiments will so fully reveal the general nature of the embodiments herein that others can, by applying current knowledge, readily modify and/or adapt for various applications such as specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modifications. However, all such modifications are deemed to be within the scope of the claims.

The embodiments herein provide a system and method for an automated apparatus for the gross examination of tissue sample. The embodiments herein enable an accurate pathological dissection to obtain the samples of ideal and relevant areas for processing. The automated apparatus also increases accuracy and reduces false-positive and false-negative results.

The automated apparatus helps a pathologist to navigate to accurate and relevant zones in the specimen. The output of present embodiment's analysis is fed to a robotic arm, which has three-dimensional blades for precise detection and dissection of the specimen to required sizes.

The embodiments herein provide a system for high speed and automated Grossing-in of specimens, to reduce the turn-around time.

The embodiments herein provide a system and method to enable better lymph node harvesting technology, which is an important event in the grossing in as the majority of the technicians are semi-skilled and under trained. The embodiments herein also assist the pathologists to enable better lymph node harvesting technology with the help of imaging and robotics techniques.

The embodiments herein provide a system and method to provide reproducible results, with objective parameters and objectification of currently subjective issues with minimum human interface and maximum accuracy.

The embodiments herein provides access to technologically qualified inputs to serve the remote areas, which largely depend on tele-pathology and where grossing in errors lead to major misdiagnosis.

The embodiments herein provide a system to enable grossing of high volumes of specimens in limited time with limited resources.

The embodiments herein provide a system and method to enable accurate measurement and to prevent cross contamination with help of automated and standardized procedures.

The embodiments herein provide system and method to enable digital documentation of the grossing process for review and corrections.

The embodiments herein provide system and method to enable better and uniform reporting of grossing-in processes and results through artificial intelligence techniques.

The embodiments herein reduce the risk accidental infection to pathologist/technicians during grossing. The embodiments herein further reduce skin and eye infections due to exposure to formalin.

The apparatus herein is configured to significantly increase accuracy in slicing the specimen and preserve the integrity of gross specimen. The apparatus is configured to avoid a lot of problems in grossing like wrong depth during splicing, which are errors due inability to understand resistivity and hardness of the specimens and increase the ability to reach deep areas which are otherwise difficult to reach such as areas close to vessels, deep lungs, intramural tumors etc.

It is also to be understood that the following claims are intended to cover all of the generic and specific features of the embodiments described herein and all the statements of the scope of the embodiments which as a matter of language might be said to fall there between.

What is claimed is:

1. A system for automatic gross-examination of tissue samples, the system comprising:
    a stainless steel bed for placing a tissue sample;
    a piezoelectric glass lid mounted on the top of the stainless steel bed;
    a robotic arm, wherein the robotic arm comprises a plurality of surgical blades and wherein the surgical blades are configured to accurately slice a tumor specimen for analysis;
    a plurality of cameras configured to take videographs of the tumor specimen;
    an ultrasound cleaning mechanism, and wherein the ultrasound cleaning mechanism is provided to keep a plurality of instruments clean for a sequential processing;
    a server; and
    an ultrasound equipment mounted on top of the stainless steel bed for detecting a size and a dimension of the tumor specimen, and wherein the ultrasound equipment is also configured to automate a process of cutting the tumor specimen;
    wherein the server is configured to perform an analysis based on artificial intelligence and machine learning technologies and a result of the analysis is are communicated from the server, and wherein the server is configured to employ a plurality of classification and supervised learning algorithms or models and digital pathology for collaboration in the analysis of the samples, and wherein an artificial intelligence engine is provided in the server for classification, probabilistic modeling and advanced image analysis of gross-examination of tissues, and wherein the analytical models are specific and customized to each type of specimen being handled, and wherein a plurality of processes comprising automated image analysis, remote viewing, pathologists' collaboration, standard image segmentation and storage retrieval are included as a part of integrated applications.

2. The system according to claim 1, wherein the stainless steel bed is provided with a disposable cover for each specimen, and wherein the bed is configured to slide out to avoid accidental injury, and wherein a box with a modular design is provided to cover the bed and wherein the box is provided with lock-in mechanisms to ensure that all the parts are opened for enabling a manual cleaning process.

3. The system according to claim 1, wherein the robotic arm capable of moving in X-axis Y-axis and Z- axis is fixed to the top of the box, and wherein the blades are configured to extend out during a dissection process and are retracted back inside the arm when not in use, and wherein the camera is mounted on a 3D movable arm for accurate capturing of the image for the detailing of the specimen, and wherein the plurality of cameras is provided to capture the details of the specimen to be grossed.

4. The system according to claim 1, wherein the robotic arm, is configured to receive an output of the ultrasound equipment and to cut and slice the sample for analysis based on a command issued from the server after an analysis by the pathologist and analytics from the server, and wherein the robotic arm, is also configured for precise detection and dissection of specimen into cubes of preset sizes using the medical grade blades based on the output from the ultrasound equipement, and wherein the cubes are transferred with help of robotic arm into an automatic wax block for preparation, which are then subjected to analysis.

5. The system according to claim 1, wherein the plurality of cameras provides one or more images and the one or more images are analyzed through an image analysis of a gross-examination sample comprising the following steps: an analysis of the specimen is carried out by the ultrasound waves and the waves are converted into coordinates by a computer algorithm; an image is captured by a piezoelectric device with the help of ultrasound waves and the image is sent to the image analysis algorithm for further analysis; a total size of the tumor versus the total size of the specimen is identified from the sonic imaging and the location of the tumor is identified with respect to its boundaries from left to right; a size of the tumor as per general slicing is also captured and stored for further use and the lymph nodes are counted from the image analysis and are mapped to the co-ordinates and nodal dissection takes place; and, the specimen is sliced from left to right while enabling more slicing at the boundaries of the tumor and while slicing the tumor, the grittiness and the texture of the tumor are captured.

6. The system according to claim 5, wherein once the slicing is done, the robotic arm disengages and the tumor is held for further clinical purposes; and wherein the tumor is then dissected to obtain a block of tumor by the robotic arm as per the grossing principles; a predefined full report is generated with all the necessary information; and, the report and the block are sent for further clinical purposes.

* * * * *